(12) United States Patent  (10) Patent No.: US 7,566,171 B2
Fuhrmann  (45) Date of Patent: Jul. 28, 2009

(54) DEVICE FOR RECORDING PROJECTION IMAGES

(75) Inventor: Michael Fuhrmann, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/217,055

(22) Filed: Jul. 1, 2008

(65) Prior Publication Data

US 2009/0010383 A1 Jan. 8, 2009

(30) Foreign Application Priority Data

Jul. 6, 2007 (DE) .................. 10 2007 031 475

(51) Int. Cl.
*H05G 1/02* (2006.01)
(52) U.S. Cl. ...................................... 378/197
(58) Field of Classification Search .......... 378/193–198
See application file for complete search history.

(56) References Cited

U.S. PATENT DOCUMENTS

| 4,807,273 A | * | 2/1989 | Haendle | 378/197 |
| 4,894,855 A | * | 1/1990 | Kresse | 378/196 |
| 6,200,024 B1 | | 3/2001 | Negrelli | 378/197 |
| 6,435,715 B1 | * | 8/2002 | Betz et al. | 378/197 |

FOREIGN PATENT DOCUMENTS

| DE | 102005012700 A1 | 8/2006 |
| DE | 102005018326 A1 | 11/2006 |
| EP | 0373596 A1 | 6/1990 |
| EP | 1306053 A2 | 5/2003 |

* cited by examiner

*Primary Examiner*—Courtney Thomas

(57) ABSTRACT

A device for recording projection images using high-energy radiation has a radiation source and a radiation detector. A radiation axis of the X-ray system can be freely established. A control device for the X-ray system enables the distance between the radiation source and radiation detector to be set with the aid of a control element set up for controlling a motion with one degree of freedom.

12 Claims, 3 Drawing Sheets

DEVICE FOR RECORDING PROJECTION IMAGES

CROSS REFERENCE TO RELATED APPLICATIONS

This application claims priority of German application No. 10 2007 031 475.4 filed Jul. 6, 2007, which is incorporated by reference herein in its entirety.

FIELD OF THE INVENTION

The invention relates to a device for recording projection images using high-energy radiation.

BACKGROUND OF THE INVENTION

A device of said type is known from EP 0 373 596 A1. The known device has an X-ray tube attached to a ceiling-mounted support. The X-ray tube can be height-adjusted via the ceiling-mounted support. It is furthermore possible to move the ceiling-mounted support longitudinally and transversally along guide paths. The known device furthermore has an X-ray detector integrated oriented horizontally in a patient examination table. A further vertically oriented X-ray detector is secured to a detector support. The distance between the X-ray tube's focal point and the plane of the X-ray detectors can be set by moving the ceiling-mounted support to which the X-ray tube is attached. The distance between the X-ray tube's focal point and the respective X-ray detector's plane is referred to also as SID (=Source-Image Distance). It is furthermore possible to move the patient examination table relative to the X-ray tube.

Projection images of all parts of a recumbent patient's body can be recorded by means of the known devices. A patient's upper body can furthermore be X-rayed with the aid of the vertically oriented X-ray detector.

A disadvantage of the known device is that patients can be X-rayed only while standing or lying. However, it is occasionally also necessary to record X-ray images of patients in other positions. For recordings of such type it may be necessary for the detector plane to assume a position other than the horizontal or vertical. Such X-ray recordings cannot be made using the known device.

SUMMARY OF THE INVENTION

The object of the invention, proceeding from said prior art, is to provide a device that is designed for recording projection images using high-energy radiation and is flexible in its orientation and easy to operate.

Said object is achieved by means of a device having the features of the independent claim. Advantageous embodiments and developments are indicated in claims dependent thereon.

The device comprises:
a movable radiation source that is attached to a radiation emitter mount and emits high-energy radiation along a radiation axis,
a movable radiation detector attached to a detector mount, and
a control device that controls the motion of the radiation source and radiation detector.

In the device the radiation source emits high-energy radiation along a radiation axis. The radiation axis can in the device be established in a spatial position other than the horizontal or vertical. The possible motion of the radiation source can furthermore be restricted to a motion along the established radiation axis. It is consequently initially possible to record projection images along a radiation axis other than the horizontal or vertical. If the distance between the radiation source and detector has to be varied while that is being done, only a one-dimensional motion along the radiation axis will need to be executed. To be able to continuously vary the distance between the radiation source and radiation detector it will not therefore be necessary for the user to execute a complex motion along a plurality of axes of motion. The distance essential between the radiation source and radiation detector for recording projection images will accordingly be easy to set despite the radiation axis' being in a position other than the vertical or horizontal and the device will hence be easy to operate.

In a preferred embodiment variant, the possible motion of the radiation detector can be additionally restricted to motions in a direction at right angles to the radiation axis. In said embodiment of the device there will be no change in the distance between the radiation source and radiation detector if the radiation detector is moved. It will consequently be unnecessary if the radiation detector is moved for the radiation source to be moved compliantly in order to maintain the distance between the radiation source and radiation detector.

In a further preferred embodiment variant, the radiation source and radiation detector can be swiveled around at least one rotational axis. The radiation axis can in this way be set to a position other than the horizontal or vertical.

The control device is preferably provided with an operating device that is set up for controlling a one-dimensional motion along the radiation axis and by means of which the relative motion between the radiation source and radiation detector along the radiation axis can be controlled. The user will then be able to set the distance between the radiation source and radiation detector through specifying of a desired value for the distance between the radiation source and radiation detector and automatic setting of the specified distance between the radiation source and radiation detector by the control device, or through the user's initiating a—from his/her viewpoint—one-dimensional relative motion between the radiation source and radiation detector.

The radiation source and radiation detector are preferably mounted swivelably and movably on ceiling-mounted supports. This will ensure a large measure of flexibility in orienting the radiation axis.

Motion along the radiation axis can be produced manually or in a power-assisted or motorized manner. If it is produced manually then as a rule no measures will need to be provided for preventing a collision between the radiation source and radiation detector since the user will generally discern an impending collision and avoid it. The force expended in moving the radiation source can furthermore be reduced by means of power assistance. Finally, motorized motion along the radiation axis will enable the motion of the radiation source and radiation detector to be remotely controlled.

BRIEF DESCRIPTION OF THE DRAWINGS

Further advantages and characteristics of the invention will emerge from the following description in which exemplary embodiments of the invention are described in detail with reference to the attached drawing, in which.

DETAILED DESCRIPTION OF THE INVENTION

Figure 1:
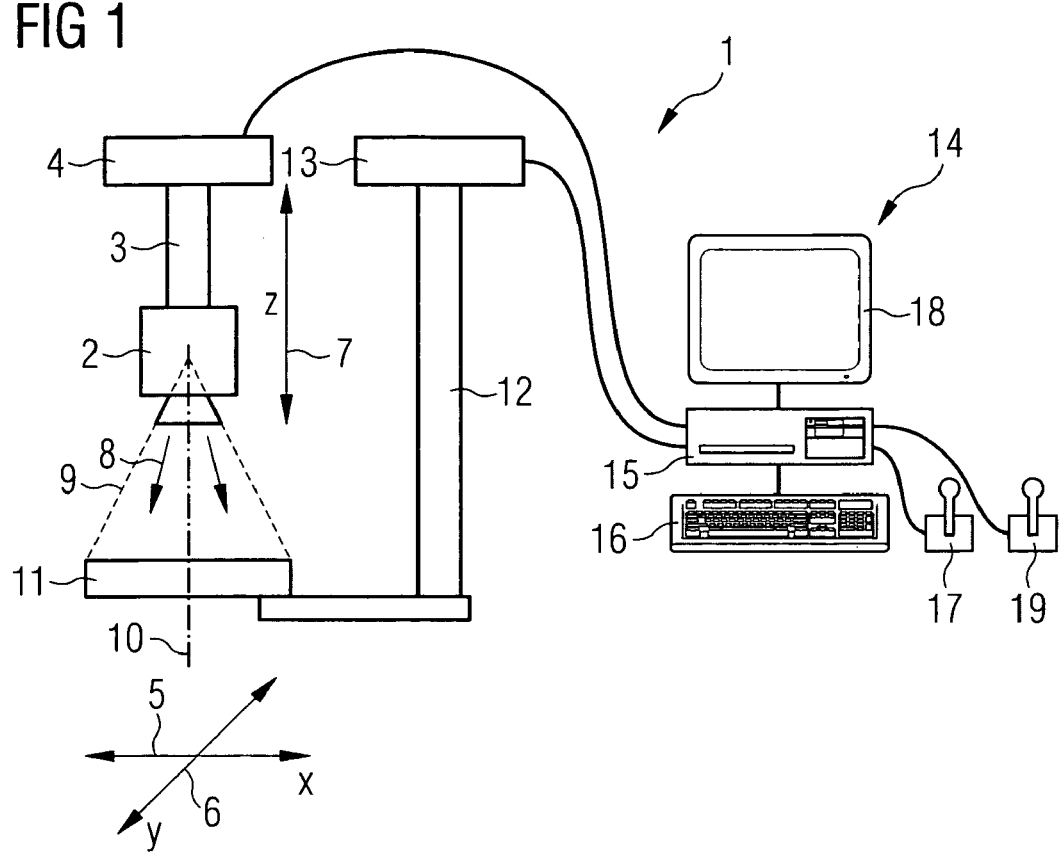
FIG. 1 shows a ceiling-mounted X-ray system having a vertically oriented radiation axis.

FIG. 1 shows an X-ray system 1 that has an X-ray tube 2. The X-ray tube 2 is attached to a radiation emitter support 3 attached in turn to the ceiling in an examination room via a mount 4. The mount 4 can be moved along a longitudinal axis 5 and along a transversal axis 6. The longitudinal axis 5 is below referred to also as the x axis and the transversal axis 6 as the y axis. The X-ray tube 2 can furthermore be moved via the radiation emitter support 3 along a height axis 7 referred to below also as the z axis.

The X-ray tube 2 emits X-radiation 8 in a radiation cone 9 whose longitudinal axis is referred to as the radiation axis 10.

The X-radiation 8 emitted by the X-ray tube 2 impinges on an X-ray detector 11 oriented relative to the X-ray tube 2 such that the radiation axis 10 of the radiation cone 9 is at right angles to the X-ray detector 11. Furthermore, the distance between the X-ray tube 2 and X-ray detector 11 is as a rule selected such that the region of the body being examined will be irradiated with X-radiation 8 but that surrounding tissue will not be exposed to X-radiation 8. For example, the height of the radiation cone 9 can be selected as the measure for the distance between the X-ray tube 2 and X-ray detector 11. The height of the radiation cone 9 is in particular the same as the distance between the focal spot on the anode of the X-ray tube 2 and the X-ray detector 11.

The X-ray detector 11 is for its part attached to a detector support 12 attached in turn to the ceiling in the examination room via a mount 13. The mount 13 of the detector support 12 can be moved as can the mount 4 of the radiation emitter support 3 along the longitudinal axis 5 or the transversal axis 6. It is furthermore possible to attach the X-ray detector 11 movably to the detector support 12 so that the X-ray detector 11 can execute a relative motion with respect to the detector support 12 along the longitudinal axis 5 and the transversal axis 6.

FIG. 1 shows the X-ray system 1 in a position provided for X-ray recordings on recumbent patients. Patients can during said recordings be lying on a patient examination table, not shown in FIG. 1, that is disposed between the X-ray tube 2 and X-ray detector 11. Provided for controlling the X-ray tube 2 and X-ray detector 11 as well as for controlling the motion of the radiation emitter support 3, the mount 4, the detector support 12, and the mount 13 is a control unit 14 which includes inter alia a computer 15 on which programs provided for controlling the X-ray system 1 run. Input devices such as, for instance, a keyboard 16 or joysticks 17 and 19 are connected to the computer 15. The control unit 14 furthermore has a display 18 that can be used for displaying input masks for presenting data, in particular for visualizing the operating status of the X-ray system, or for displaying X-ray images recorded using the X-ray detector 11.

The motion of the X-ray tube 2 along the radiation axis 10 can be controlled inter alia with the aid of the input devices in order to set the distance between the X-ray tube 2 and X-ray detector 11. In the case shown in FIG. 1, the motion along the radiation axis 10 is the same as a motion along the height axis 7. Said motion can be controlled with the aid of, for instance, the joystick 17, with said joystick having the function of a proportional controller in the case of which the speed of motion is proportional to the movement of the joystick 17. In this case the direction of motion can have been established by the direction of movement relative to a zero position. It is also possible for the user to enter a desired value for the distance between the X-ray tube 2 and X-ray detector 11 via the keyboard 16 in an input field displayed on the display 18 and for the computer 15 to cause the X-ray tube 2 to move until the desired value for the distance between the X-ray tube 2 and X-ray detector 11 has been attained.

The X-ray detector 11 can also be moved with the aid of the joystick 17 or keyboard 16. The function of the joystick 17 can be switched over when that is done, or an additional control element that is provided exclusively for controlling the motion of the X-ray detector 11 can be provided for controlling the motion of the X-ray detector 11. Said additional control element can be, for example, the further joystick 19 shown in FIG. 1, with a movement along the longitudinal axis 5 resulting in a motion along the longitudinal axis 5 and a movement along the transversal axis 6 causing a motion along the transversal axis 6. The direction of movement relative to a zero position can here, too, establish the direction of motion.

Figure 2:
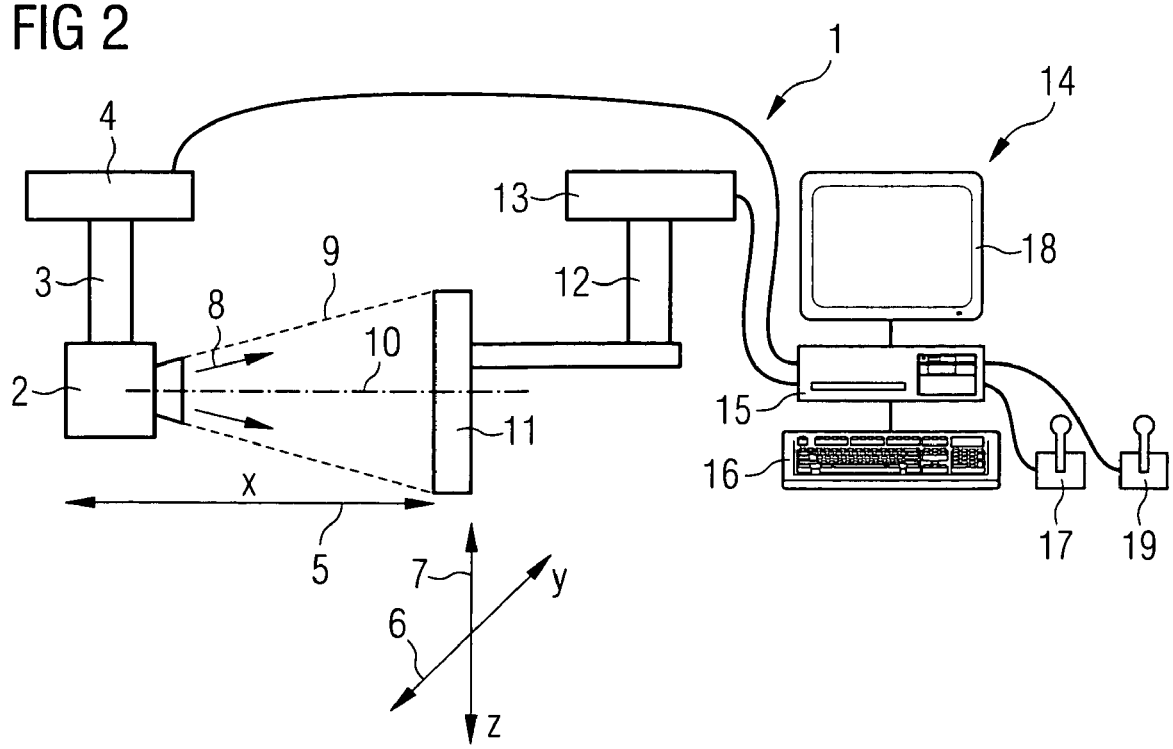
FIG. 2 shows the X-ray system shown in FIG. 1 having a horizontally oriented radiation axis.

FIG. 2 shows the case in which the X-ray system 1 has been oriented for producing an X-ray recording on a standing patient. In particular the X-ray tube 2 has been swiveled around a rotational axis so that the radiation axis 10 is in the horizontal direction. For this purpose at least one rotational axis must be provided on the radiation emitter support 3. However, the radiation emitter support 3 preferably has at least two rotational axes, for example a rotational axis which in the case of the position shown in FIG. 1 is in the y direction and a further rotational axis around the z axis.

Compared with FIG. 1, in FIG. 2 the X-ray detector 11 has been swiveled around a rotational axis of the detector support 12 so that the surface normal of the X-ray detector 11 is oriented horizontally. Like the radiation emitter support 3, the detector support 12 can also be provided with a plurality of rotational axes.

The control unit 14 now enables the distance between the X-ray tube 2 and X-ray detector 11 to be set by means of the same movement of the joystick 17 as in the situation shown in FIG. 1. Thus, in the case shown in FIG. 2, the radiation emitter support 3 is not extended or retracted along the height axis 7; the X-ray tube 2 is instead moved along the longitudinal axis 5. The joystick 17 thus no longer acts upon a drive motor for changing the height position of the X-ray tube 2 but upon a drive motor for moving the mount 4 along the longitudinal axis 5. The joystick 19 provided for moving the X-ray detector similarly acts upon positioning motors that move the X-ray detector 11 along the height axis 7 and transversal axis 6. The X-ray detector 11 will be moved along the transversal axis 6 while the joystick 19 is being moved along the transversal axis 6; moving said joystick along the longitudinal axis 5 will cause the X-ray detector 11 to move along the height axis 11.

Figure 3:
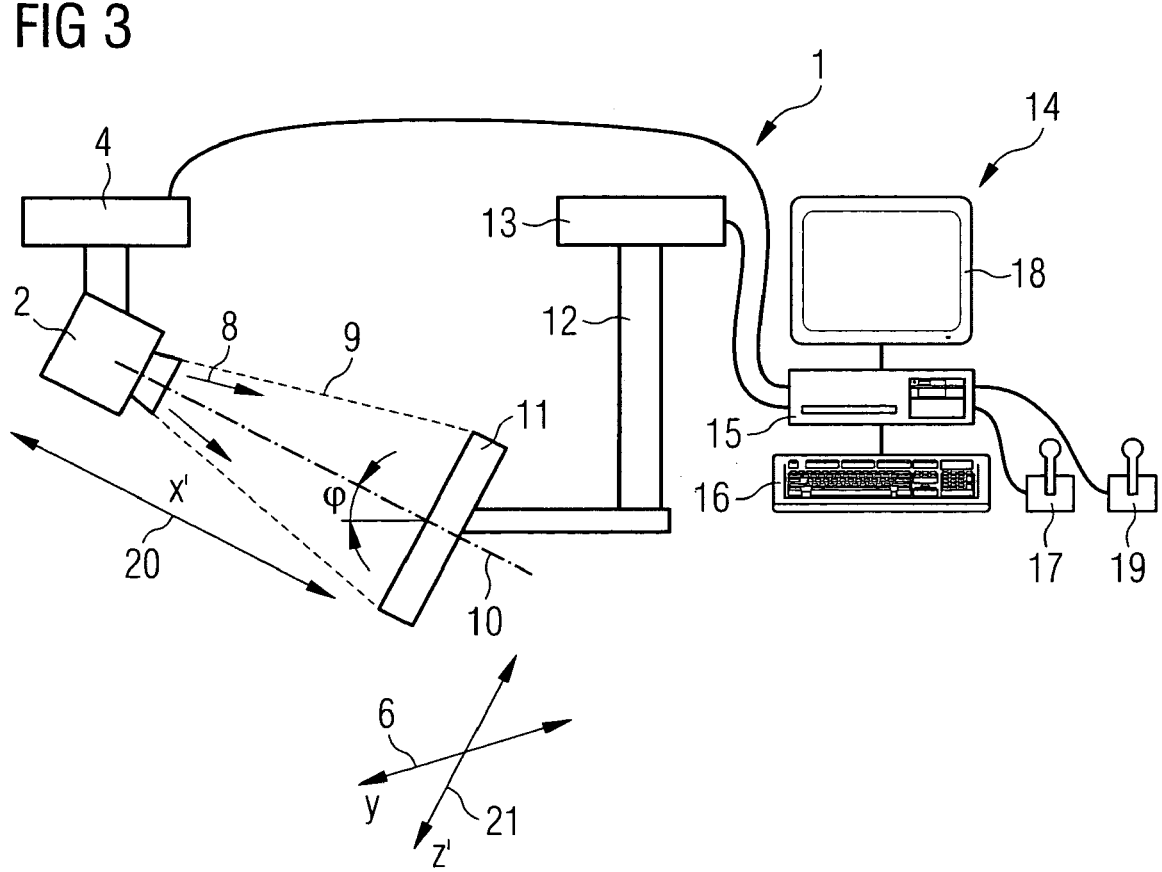
FIG. 3 shows the X-ray system shown in FIGS. 1 and 2 having a radiation axis inclined relative to the horizontal.

Further shown in FIG. 3 is the case in which the radiation axis 10 assumes an angle $\phi$ with respect to the horizontal. In that case, too, the distance between the X-ray tube 2 and X-ray detector 11 can be set with the aid of the joystick 17, which will then act upon positioning motors that move the X-ray tube 2 along the radiation axis 10. The X-ray tube 2 must therefore be moved simultaneously along the height axis 7 and longitudinal axis 5 so that the X-ray tube 2 can move along an inclined longitudinal axis 20. To move the X-ray detector 11 along the transversal axis 6 and an inclined height axis 21 that is at right angles to the inclined longitudinal axis 20, the joystick 19 is provided which when moved will cause the X-ray detector 11 to be moved along the transversal axis 6 and inclined height axis 21.

Figure 4:
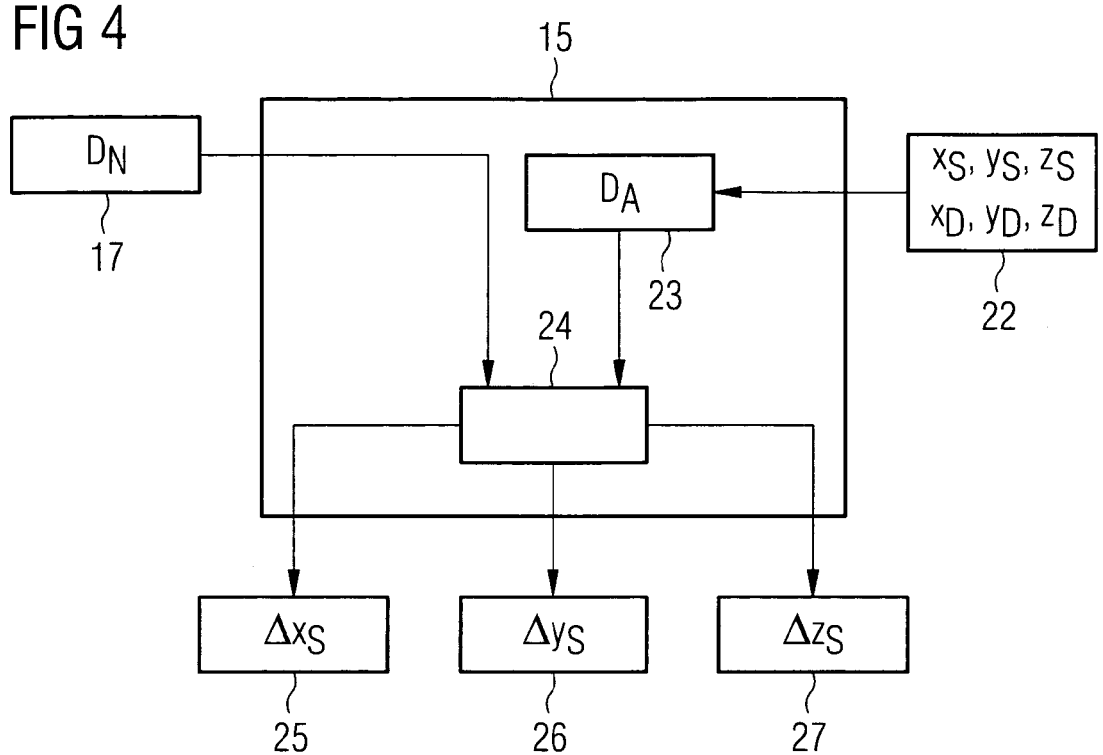
FIG. 4 is a block diagram of a control means for setting the distance between an X-ray tube and X-ray detector belonging to the X-ray system shown in FIGS. 1 to 3.

FIG. 4 is a block diagram of a control device for controlling the distance D between the X-ray tube 2 and X-ray detector 11. A desired distance $D_N$ is specified with the aid of the joystick 17. The current position $(x_S, y_S, z_S)$ of the X-ray tube 2 and the position $(x_D, y_D, z_D)$ of the X-ray detector 11 are furthermore determined by way of position sensors 22 and fed to a distance unit 23, which from the positional information determines the current distance $D_A$ between the X-ray tube 2 and X-ray detector 1. The desired distance $D_N$ and current distance $D_A$ are fed to an adjusting unit 24, which applies control signals to positioning motors 25, 26, and 27. The X-ray tube 2 is moved by the positioning motors 25, 26, and 27 along the longitudinal axis 5 by $\Delta x_S$, along the transversal axis 6 by $\Delta y_S$, and along the height axis by $\Delta z_S$.

Figure 5:
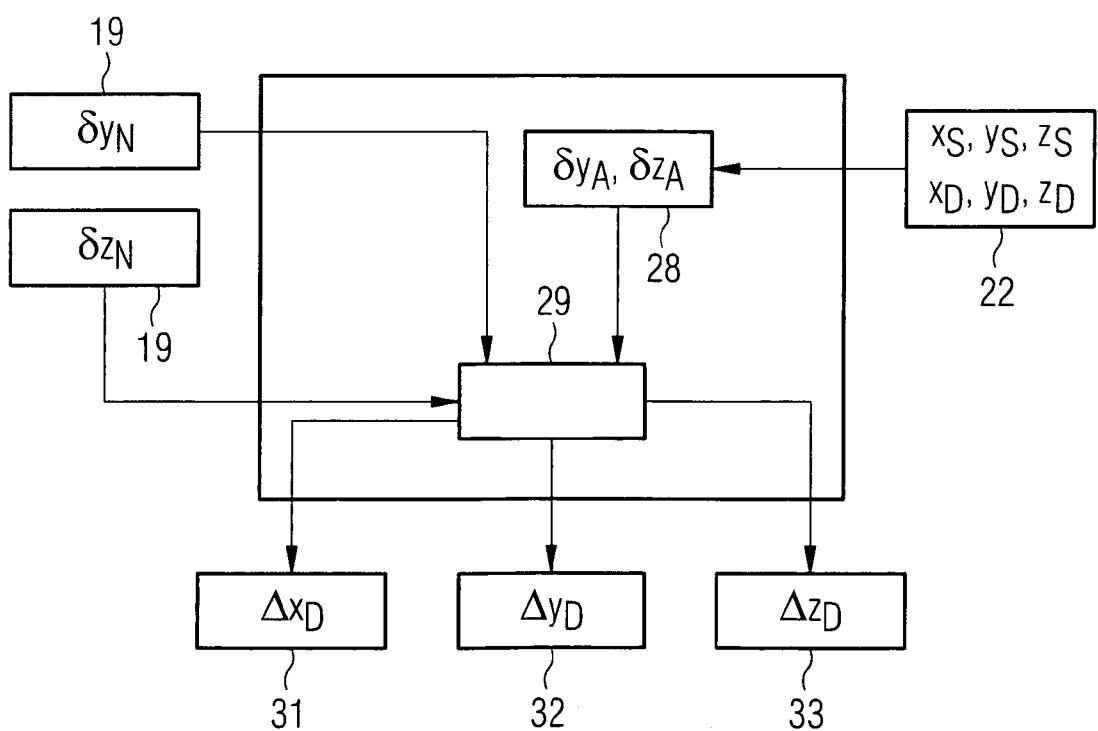
FIG. 5 is a block diagram showing controlling of the motion of the X-ray detector of the X-ray system shown in FIGS. 1 and 3 across the radiation axis.

FIG. 5, finally, is a block diagram showing how the motion of the X-ray detector 11 is controlled. The desired values $\delta y_N$ and $\delta z_N$ for the X-ray detector's position relative to the radiation axis 10 are specified with the aid of the joystick 19. The position sensors 22 furthermore feed a position unit 28, which from the position values $(x_S, y_S, z_S)$ of the X-ray tube 2 and from the position data $(x_D, y_D, z_D)$ of the X-ray detector 11 determines the current position $(\delta y_A, \delta z_A)$ of the X-ray detector 11 relative to the radiation axis 10. The desired values $(\delta y_N, \delta z_N)$ fed out by the joystick 19 are fed along with the current positional values $(\delta y_A, \delta z_A)$ to an adjusting unit 29 which applies control signals that vary the position of the X-ray detector 11 along the longitudinal axis 5 by $\Delta x_D$, along the transversal axis 6 by $\Delta y_D$, and along the height axis 7 by $\Delta z_D$ to the positioning motors 30, 31, and 32.

Let it be noted that other control elements, for example pushbuttons for different directions of motion, can also be provided in place of the joysticks 17 and 19. What can further be considered is entering the desired distance between the X-ray detector 11 and X-ray tube 2 and the position of the X-ray detector 11 relative to the radiation axis by entering a desired value via the keyboard 16 in an entry field displayed on the display 18.

Irrespective of the control means used, the X-ray system 1 described here has the advantage that the distance between the X-ray tube 2 and X-ray detector 11 is varied through a motion that is one-dimensional from the user's viewpoint. The user is therefore offered just one degree of freedom, which is why the X-ray system 1 can be operated in a simple manner. The user is similarly offered only two degrees of freedom for moving the X-ray detector 11 so that the X-ray detector 11 can also be moved in a simple manner.

Attention is further drawn to the possibility also of providing a motion of the X-ray detector 11 for shortening the distance between the X-ray tube 2 and X-ray detector 11. This will be necessary in particular if only swiveling movements can be executed by means of the X-ray tube 2.

The X-ray detector 11 and X-ray tube 2 can also be moved manually or in a power-assisted manner. If they are moved manually or in a power-assisted manner then positioning motors will insure that freewheeling with one degree of freedom along the radiation axis 10 is available to the user for setting the distance between the X-ray detector 11 and X-ray tube 2. The same applies to motion across the radiation axis 10, which motion can likewise be executed in a power-assisted manner or manually. However, only a motion having two degrees of freedom at right angles to the radiation axis is permitted when that is done.

Attention is finally drawn to the fact that features and characteristics described in connection with a specific exemplary embodiment can also be combined with another exemplary embodiment except when that is precluded for compatibility reasons.

Attention is in conclusion drawn also to the fact that in the claims and in the description the singular form also includes the plural form, except when the context dictates otherwise. Both the singular and the plural forms are intended particularly when the indefinite article is used.

The invention claimed is:

1. A device for recording a projection image, comprising:
   a radiation emitter mount;
   a radiation source attached to the radiation emitter mount that emits high-energy radiation along a radiation axis being set up in a spatial position comprising a non-horizontal position or a non-vertical position and is restricted to a movement along the radiation axis;
   a detector mount;
   a radiation detector attached to the detector mount that records the projection image; and
   a control device that controls the movement of the radiation source and a movement of the radiation detector so that a relative movement between the radiation source and the radiation detector is restricted along the radiation axis.

2. The device as claimed in claim 1, wherein the movement of the radiation detector is restricted across the radiation axis.

3. The device as claimed in claim 2, wherein the movement of the radiation detector is restricted to perpendicular to the radiation axis.

4. The device as claimed in claim 1, wherein the radiation source is moved or swiveled via the radiation emitter mount.

5. The device as claimed in claim 1, wherein the radiation detector is moved or swiveled via the detector mount.

6. The device as claimed in claim 1, wherein the relative movement between the radiation source and the radiation detector along the radiation axis is one degree of freedom.

7. The device as claimed in claim 1, wherein the movement of the radiation detector is two degrees of freedom.

8. The device as claimed in claim 1, wherein the radiation source is moved motorizedly, power-assistedly, or manually.

9. The device as claimed in claim 1, wherein the radiation detector is moved motorizedly, power-assistedly, or manually.

10. The device as claimed in claim 1, wherein the radiation source is attached to a ceiling-mounted support.

11. The device as claimed in claim 1, wherein the radiation detector is attached to a ceiling-mounted support.

12. A method for operating an imaging device, comprising:
    emitting high-energy radiation from a radiation source of the imaging device to a radiation detector of the image device along a radiation axis;
    setting up the radiation axis in a spatial position comprising a non-horizontal position or a non-vertical position;
    restricting a movement of the radiation source along the radiation axis; and
    restricting a relative movement between the radiation source and the radiation detector along the radiation axis.

* * * * *